United States Patent
Sheu et al.

(10) Patent No.: US 11,571,476 B2
(45) Date of Patent: Feb. 7, 2023

(54) ANTI-TUMOR/ANTI-TUMOR ASSOCIATED FIBROBLAST/ANTI-HAPTEN TRISPECIFIC ANTIBODIES AND USE THEREOF

(71) Applicant: TAIPEI MEDICAL UNIVERSITY, Taipei (TW)

(72) Inventors: Ming-Thau Sheu, Taipei (TW); Yuan-Soon Ho, New Taipei (TW); Kuo-Hsiang Chuang, New Taipei (TW); Michael Chen, Hsinchu County (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 466 days.

(21) Appl. No.: 15/837,908

(22) Filed: Dec. 11, 2017

(65) Prior Publication Data

US 2019/0175732 A1 Jun. 13, 2019

(51) Int. Cl.
| | | |
|---|---|---|
| C07K 16/00 | (2006.01) | |
| A61K 39/395 | (2006.01) | |
| A61P 35/00 | (2006.01) | |
| A61K 47/68 | (2017.01) | |
| C07K 16/30 | (2006.01) | |
| C07K 16/32 | (2006.01) | |
| C07K 16/40 | (2006.01) | |
| C07K 16/28 | (2006.01) | |
| A61K 47/69 | (2017.01) | |
| C07K 16/44 | (2006.01) | |
| A61K 39/00 | (2006.01) | |

(52) U.S. Cl.
CPC .... *A61K 39/39558* (2013.01); *A61K 39/3955* (2013.01); *A61K 47/6855* (2017.08); *A61K 47/6869* (2017.08); *A61K 47/6913* (2017.08); *A61P 35/00* (2018.01); *C07K 16/2863* (2013.01); *C07K 16/3069* (2013.01); *C07K 16/32* (2013.01); *C07K 16/40* (2013.01); *C07K 16/44* (2013.01); *A61K 2039/505* (2013.01); *A61K 2039/507* (2013.01); *C07K 2317/31* (2013.01); *C07K 2317/622* (2013.01)

(58) Field of Classification Search
CPC .......... A61K 39/39558; A61K 47/6855; A61K 2039/505; A61P 35/00; C07K 2317/31
See application file for complete search history.

(56) References Cited

U.S. PATENT DOCUMENTS

| | | | |
|---|---|---|---|
| 8,568,727 B2 | 10/2013 | Adolf et al. | |
| 2003/0162709 A1 | 8/2003 | Rossi et al. | |
| 2005/0129752 A1 | 6/2005 | Chen et al. | |
| 2016/0355600 A1* | 12/2016 | Moore | C07K 16/2809 |

FOREIGN PATENT DOCUMENTS

WO WO2015134411 9/2015

OTHER PUBLICATIONS

Office Action and Search Report dated Sep. 27, 2018 issued by Taiwan Intellectual Property Office (TIPO) for counterpart application 106143621.
English Translated Search Report issued by Taiwan Intellectual Property Office (TIPO) for counterpart application 106143621.
English Translated Abstract Summary of Office Action issued by Taiwan Intellectual Property Office (TIPO) for counterpart application 106143621.
Tansi et al., "Activatable bispecific liposomes bearing fibroblast activation protein directed single chain fragment/Trastuzumab deliver encapsulated cargo into the nuclei of tumor cells and the tumor microenvironment simultaneously" Acta Biomaterialia 54 (2017) 281-293, Available online Mar. 24, 2017.
Kao et al., "One-step mixing with humanized anti-mPEG bispecific antibody enhances tumor accumulation and therapeutic efficacy of mPEGylated nanoparticles" Biomaterials 35 (2014) 9930e9940.
Sheu et al., "Design and Preclinical Translation Study of Mixed Bispecific/Trispecific Antibody for Enhancing Therapeutic Effectiveness of Anticancer Drug-Loaded Pegylated Nanocarriers by Simultaneously Targeting to Tumor Cells and Cancer/Tumor Associated Fibrobla" Taipei Medical University project (https://tmu.pure.elsevier.com/en/projects/design-and-preclinical-translation-study-of-mixedbispecifictrisp-2); publication date: Jul. 31, 2016.

* cited by examiner

*Primary Examiner* — Mark Halvorson
(74) *Attorney, Agent, or Firm* — WPAT, P.C., Intellectual Property Attorneys; Anthony King (57) ABSTRACT

The present invention relates to an anti-tumor/anti-tumor-associated fibroblast (TAF)/anti-hapten trispecific antibody (TsAb). The anti-hapten domain enables TsAb to arm various hapten-conjugated anti-cancer drugs (nanocarrier drugs, small molecule drugs, protein drugs, and radioactive drugs). The anti-tumor domain enables TsAb-armed drugs to target tumor cells, while the anti-TAF domain enables the TsAb-armed drugs to target TAFs. The present invention allows the simultaneous killing of tumor cells and TAFs by various drugs through arming with TsAb.

12 Claims, 11 Drawing Sheets

ANTI-TUMOR/ANTI-TUMOR ASSOCIATED FIBROBLAST/ANTI-HAPTEN TRISPECIFIC ANTIBODIES AND USE THEREOF

FIELD OF THE INVENTION

The present invention relates to a field of antibody against a tumor. Particularly, the present invention pertains to a trispecific antibody against a tumor.

BACKGROUND OF THE INVENTION

Malignant solid tumors have been commonly treated by surgery, chemotherapy, and radiation. These approaches are sometimes only palliative. Recent efforts to treat malignant solid tumors have applied immunomodulatory strategies, including administration of genetically modified tumor cells, dendritic cells either pulsed or transduced with tumor-associated antigens, immunization with soluble proteins or synthetic peptides, recombinant viruses or bacteria encoding tumor-associated antigens, and naked plasmid DNA encoding tumor-associated antigens. Nanoparticle compositions have been developed as a drug delivery system for delivering an anti-cancer drug to the desired tissues or cells.

US 20050129752 provides a method of treating mammals having pancreatic cancer by administering a liposomal doxorubicin pharmaceutical composition, and a process of manufacturing the composition. U.S. Pat. No. 9,226,966 discloses methods for determining dosage of HER2-targeted anthracycline-containing immunoliposomes. WO 2015134411 discloses a bi-specific antibody that specifically directs a therapeutic agent to a cancer cell by targeting a tumor antigen of the cancer cell, and thereby suppresses the growth of the cancer or blocking the invasion or metastasis of the cancer. The bi-specific antibody includes a first antigen binding site that binds to polyethylene glycol (PEG); and a second antigen binding site that binds to a target ligand such as a tumor antigen.

It is well-recognized that the tumor micro-environment plays a primary role in determining tumor progression and metastasis in many different types of epithelial cancers. In this regard, "activated or myofibroblastic" cancer-associated fibroblast have emerged as one of the most prominent cell types in the tumor stroma that may determine clinical outcome in cancers.

A cancer-associated fibroblast (CAF) (also known as tumor-associated fibroblast; carcinogenic-associated fibroblast; activated fibroblast) is a cell type within the tumor microenvironment that promotes tumorigenic features by initiating the remodeling of the extracellular matrix or by secreting cytokines. The functions of these CAFs (TAFs) have been known to stimulate angiogenesis, supporting the formation of tumors and thus proliferation of cancer cell and metastasis. These TAFs actively interact with neoplastic cells and form a myofibroblastic microenvironment that promotes cancer growth and survival and supports malignancy. Due to the broad expression of Fibroblast Activation Protein (FAP) in many common cancers and its restricted expression pattern in normal tissues, fibroblast activation protein alpha (FAP-α; in the following referred as FAP) has been considered to be an attractive antigenic target.

U.S. Pat. No. 8,768,727 discloses that tumor killing may be caused by targeting FAP to stromal cells due to its property of being a stromal antigen. On the other hand, it could be shown that the anti-FAP antibody maytansinoid conjugates are highly efficient in killing tumor cells in human tumor xenografts expressing FAY, an effect that could, in the chosen experiment setting, be ascribed to FAP's property of being a tumor antigen.

However, there is still a need for more effective cancer treatment.

SUMMARY OF THE INVENTION

The present invention relates to an anti-tumor/anti-tumor-associated fibroblast (TAF)/anti-hapten trispecific antibody (TsAb). The anti-hapten domain enables TsAb to arm on various hapten-conjugated anti-cancer drugs (nanocarrier drugs, small molecule drugs, protein drugs, and radioactive drugs). The anti-tumor domain enables TsAb-armed drugs to target tumor cells, while the anti-TAF domain enables the TsAb-armed drugs to target TAFs. The present invention allows the simultaneous killing of tumor cells and TAFs by various drugs through arming with TsAb.

The present invention provides a trispecific antigen-binding protein. The trispecific antigen-binding protein comprises (a) a first domain (A) that specifically binds to hapten, comprising a light chain variable region sequence (A-VL) and a heavy chain variable region sequence (A-VH); (b) a second domain (B) that specifically binds to a target tumor antigen; and (c) a third domain (C) that specifically binds to a fibroblast activation protein, wherein the domains are linked in the order $H_2N$-(A)-(C)-(B)—COOH, $H_2N$-(A)-(B)-(C)—COOH, $H_2N$-(A-VL)-(C)-(A-VH)-(B)—COOH or $H_2N$-(A-VL)-(B)-(A-VH)-(C)—COOH. The certain embodiments include the trispecific antigen-binding proteins having a domain order of $H_2N$-(A-VL)-(C)-(A-VH)-(B)—COOH and $H_2N$-(A-VL)-(B)-(A-VH)-(C)—COOH.

The first domain (A), which specifically binds to hapten, comprises a light chain variable region sequence (A-VL) and a heavy chain variable region sequence (A-VH). In some embodiments, the hapten include polyethylene glycol, methoxy polyethylene glycol, fluorescein, biotin, nitroaryls (for example, dinitrophenyl (DNP)), and digoxigenin. Additional examples of hapten include oxazole, pyrazole, thiazole, nitroaryl, benzofuran, triperpene, urea, thiourea, rotenoid, coumarin and cyclolignan haptens.

The second domain (B) of the trispecific antigen-binding protein, which specifically binds to a target tumor antigen, can be any domain that binds to a target tumor antigen including, but not limited to, domains from a monoclonal antibody, a polyclonal antibody, a recombinant antibody, a human antibody and a humanized antibody. In one embodiment, the second domain is a single chain variable fragment (scFv). In some embodiments, the second domain is from anti-human epidermal growth factor receptor 2 antibody (anti-HER2 antibody), anti-epidermal growth factor receptor antibody (anti-EGFR antibody) or anti-prostate specific membrane antigen antibody (anti-PSMA antibody). In some embodiments, the second domain is anti-HER2 scFv, anti-α-EGFR scFv or anti-PSMA scFv.

The third domain (C), which specifically binds to a fibroblast activation protein (FAP), can be any domain that binds to a FAP including, but not limited to, domains from a monoclonal antibody, a polyclonal antibody, a recombinant antibody, a human antibody, a humanized antibody. In one embodiment, the third domain is a single chain variable fragment (scFv).

The present invention provides a nanocarrier comprising a trispecific antigen-binding protein of the invention.

The present invention also provides a pharmaceutical composition comprising a trispecific antigen-binding protein or a nanocarrier of the invention and a pharmaceutically acceptable carrier.

The present invention also provides a method for treating a cancer, comprising administering a trispecific antigen-binding protein or a nanocarrier of the invention to a subject.

The present invention further provides A nanocarrier complex, comprising:
(i) a nanocarrier, optionally encapsulated with a therapeutic agent; and
(ii) a plurality of multispecific antigen-binding scFv antibody, which specifically binds to two or more target antigens and conjugate on the surface of the nanocarrier, wherein the target antigens may be the same or different.

BRIEF DESCRIPTION OF THE DRAWING

FIGS. 1A to 1C show the DNA sequences of TsAb (FIG. 1A) and BsAb (FIG. 1B and FIG. 1C). From $NH_2$ terminus to the COOH terminus, the sequence includes a signal peptide (SP), an anti-Hapten light chain (α-Hapten VL-CK), a linker peptide (L) with 15 amino acids, an anti-TAF scFv (α-TAF scFv), an internal ribosome entry site (IRES), a SP, an anti-Hapten heavy chain (α-Hapten VH—CH1), a L and an anti-Tumor scFv (α-Tumor scFv).

FIG. 2A: 12.5% of SDS-PAGE (non-reducing condition) was used in electrophoresis. FIG. 2B: 10% SDS-PAGE (non-reducing condition) was used in electrophoresis and then Coomassie blue was used in staining.

FIG. 3A: The α-HER2/α-FAP/α-mPEG TsAb, α-HER2/α-mPEG BsAb and the control BsAb were reacted with $HER2^+$ SKBR3 cells. FIG. 3B: The α-EGFR/α-mPEG BsAb and the control BsAb were reacted with $EGFR^+$ HT29 cells. FIG. 3C: The α-PSMA/α-mPEG BsAb and the control BsAb were reacted with LNCap cells. FIG. 3D: The α-FAP/α-mPEG BsAb, α-HER2/α-FAP/α-mPEG TsAb and the control BsAb were reacted with $FAP^+$ human fibroblasts (WS-1). After one hour reaction, mouse anti-His tag antibody and FITC-conjugated Goat anti-Rabbit antibody were added and the binding of BsAb and TsAb to the cell surfaces were measured by flow cytometry.

FIG. 4 shows the binding specificity and capability of BsAb to mPEG. mPEG ($CH_3O$-PEG, 10 μg/mL) or BSA (10 μg/mL) was immobilized on 96-well plate and then BsAb or TsAb, HRP-conjugated Goat anti-human IgG Fab, and ABTS were subsequently added to the plate. The absorbance was detected by ELISA reader (OD405 nm).

FIG. 5 shows the in vitro comparison of TsAb- (or BsAb-) Lipo-Dox and Lipo-Dox in killing tumor cells. The α-HER2/α-FAP/α-mPEG TsAb, α-HER2/α-mPEG BsAb and α-FAP/α-mPEG BsAb were reacted with Lipo-Dox (molar ratio of antibody:Lipo-Dox (surface with mPEG)=1:200) in DMEM solution, respectively. After one hour, the resulting reaction mixtures were added to the 96-well plate and cultured with $HER^+$ MCF7/HER2 cells at 37° C. for one hour. After 72 hours, ATPlite kit (Perkin-Elmer) and Top Count NXT (Packard Instruments Company) were used to detect the cell viability. Bar, SD.

FIG. 6 shows the in vitro comparison of TsAb- (or BsAb-) Lipo-Dox and Lipo-Dox in killing tumor-associated fibroblasts. The α-HER2/α-FAP/α-mPEG TsAb, α-HER2/α-mPEG BsAb and α-FAP/α-mPEG BsAb were reacted with Lipo-Dox (molar ratio of antibody:Lipo-Dox (surface with mPEG)=1:200) in DMEM solution, respectively. After one hour, the resulting reaction mixtures were added to the 96-well plate and cultured with FAP WS-1/FAP cells at 37° C. for one hour. After 72 hours, ATPlite kit (Perkin-Elmer) and Top Count NXT (Packard Instruments Company) were used to detect the cell viability. Bar, SD.

FIG. 10A: The α-HER2/α-FAP/α-mPEG TsAb-Lipo-Dox, α-HER2/α-mPEG BsAb-Lipo-Dox and Lipo-Dox were administered to the mice through intravenous injection, tail vein. The blood samples were taken at 10 minutes, 6 hours, 24 hours, 48 hours and 72 hours and the amounts of Lipo-Dox in vivo were measured by anti-PEG sandwich ELISA (*Bioconjugate Chemistry* 2010, 21, 1264-1270). FIG. 10B: The remaining amounts of TsAb and BsAb on the liposome at each time points were measured by anti-PEG/anti-human IgG Fab sandwich ELISA. The relative amounts of TsAb or BsAb at 6 hours, 24 hours, 48 hours and 72 hours were normalized to 10 minutes after the injection.

DETAILED DESCRIPTION OF THE INVENTION

Described herein are trispecific antigen-binding proteins and pharmaceutical compositions thereof. Also provided are methods of using the disclosed trispecific antigen-binding proteins in the prevention, and/or treatment of diseases, conditions and disorders.

Unless defined otherwise, all technical and scientific terms used herein have the same meanings as commonly understood by one of skill in the art to which the disclosed method and compositions belong. It must be noted that as used herein and in the appended claims, the singular forms "a", "an", and "the" include plural reference unless the context clearly dictates otherwise. With respect to the teachings in the present application, any issued patent, pending patent application or patent application publication described in this application is expressly incorporated by reference herein.

As used herein, the term "or" is used herein to mean, and is used interchangeably with, the term "and/or", unless context clearly indicates otherwise.

As used herein, the term "nanocarrier" refers to a nanoscale carrier with a size that is measured in nanometers, for example, a nanoscopic carrier that has at least one dimension of less than about 100 nm. Examples of nanocarrier include, but are not limited to, liposomes and micelles.

As used herein, the term "liposome" refers to vesicles comprised of one or more concentrically ordered bilayers which encapsulate an aqueous phase. The term liposome includes unilamellar vesicles comprised of a single lipid bilayer.

As used herein, the term "encapsulation" refers to encircling an internal phase typically resulting in an interior cavity separated from an external media. The components of the internal phase/interior cavity are thus "encapsulated" as described herein. As described herein, the encircled, or encapsulated, internal phase is an aqueous phase. The amount of therapeutic drug that is loaded into the interior cavity of the liposome and therefore unavailable to the external media until the liposome is triggered from release would be considered as "encapsulated" within the liposome.

As used herein, the term "antibody" refers to a polypeptide or a polypeptide complex that specifically recognizes and binds to an antigen through one or more immunoglobulin variable regions. An antibody can be a whole antibody, an antigen binding fragment or a single chain thereof.

As used herein, the term "trispecific antibody" refers to an antibody that specifically binds to three different antigen targets.

As used herein, the term "Fab" fragment is a monovalent fragment consisting of the VL, VH, CL and CH I domains; a F(ab')$_2$ fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment consists of a VH domain.

As used herein, the term "single-chain fragment variable" or "scFv" refers to an antibody fragment comprising a variable region of a light chain and a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived. In some aspects, the regions are connected with a short linker peptide of 10 to about 25 amino acids. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker.

By "specifically binds" or "has specificity to", it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope via its antigen-binding domain more readily than it would bind to a random, unrelated epitope. The term "specificity" is used herein to qualify the relative affinity by which a certain antibody binds to a certain epitope.

As used herein, the terms "treat" and "treatment" refer to the amelioration of one or more symptoms associated with a tumor or cancer, prevention or delay of the onset of one or more symptoms of a tumor or cancer; and/or lessening of the severity or frequency of one or more symptoms of tumor or cancer.

As used herein, the terms "therapeutically effective amount", "pharmacologically effective amount", and "physiologically effective amount" are used interchangeably to mean the amount of a trispecific antibody that is needed to provide a threshold level of active antagonist agents in the bloodstream or in the target tissue.

Trispecific Antigen-Binding Protein and Nanocarrier and Pharmaceutical Composition Comprising the Protein One aspect of the present application relates to a trispecific antigen-binding protein. The trispecific antigen-binding protein comprises (a) a first domain (A) that specifically binds to hapten, comprising a light chain variable region sequence (A-VL) and a heavy chain variable region sequence (A-VH); (b) a second domain (B) that specifically binds to a target tumor antigen; and (c) a third domain (C) that specifically binds to a fibroblast activation protein, wherein the domains are linked in the order H$_2$N-(A)-(C)-(B)—COOH, H$_2$N-(A)-(B)-(C)—COOH, H$_2$N-(A-VL)-(C)-(A-VH)-(B)—COOH or H$_2$N-(A-VL)-(B)-(A-VH)-(C)—COOH.

In some embodiments, the trispecific antigen-binding proteins have a domain order of H$_2$N-(A-VL)-(C)-(A-VH)-(B)—COOH. In some embodiments, the trispecific antigen-binding proteins have a domain order of H$_2$N-(A-VL)-(B)-(A-VH)-(C)—COOH. In some embodiments, the trispecific antigen-binding proteins have a domain order of H$_2$N-(A)-(C)-(B)—COOH. In some embodiments, the trispecific antigen-binding proteins have a domain order of H$_2$N-(A)-(B)-(C)—COOH.

In some embodiments, the trispecific antigen-binding protein is a trispecific antibody or an antibody fragment comprising an antigen-binding domain containing one more immunoglobulin variable regions (e.g., VH1, VH2, VL1, VL2) and their associated complementarity derived regions (CDRs) and framework regions (FRs) in immunoglobulin heavy and light chains. The antibody fragment may comprise a single polypeptide chain or a pair of polypeptide chains associated with one another. The sequences from these regions may be determined experimentally by conventional methods or they may be identified from published immunoglobulin heavy and light chain sequences.

In some embodiments, the first domain (A), which specifically binds to hapten, comprises a light chain variable region sequence (A-VL) and a heavy chain variable region sequence (A-VH). The first domain (A) may be an anti-hapten antibody or a fragment thereof. In one embodiment, the first domain (A) is an anti-hapten Fab. Hapten is a molecule, typically a small molecule that can combine specifically with an antibody but is typically substantially incapable of being immunogenic except in combination with a carrier molecule. Examples of haptens include, but are not limited to, polyethylene glycol, methoxy polyethylene glycol, dansyl hapten, fluorescein, biotin, nitroaryls (for example, dinitrophenyl (DNP)), and digoxigenin. Additional examples of hapten include oxazole, pyrazole, thiazole, nitroaryl, benzofuran, triperpene, urea, thiourea, rotenoid, coumarin and cyclolignan haptens. In one embodiment, the hapten can be converted to a nonimmunological and tolerogenic derivative by conjugation to nonimmunogenic, hydrophilic, synthetic polymers, such as mPEG, PVA, and PVP.

In some embodiments, the second domain (B) of the trispecific antigen-binding protein that specifically binds to a target tumor antigen can be any domain that binds to a target tumor antigen including, but not limited to, domains from a monoclonal antibody, a polyclonal antibody, a recombinant antibody, a human antibody and a humanized antibody. In one embodiment, the second domain is a single chain variable fragment (scFv) comprising a light chain and a heavy chain of an amino acid sequence provided herein. In one embodiment, the second domain is a scFv, and a light chain variable region comprising an amino acid sequence described herein, is attached to a heavy chain variable region comprising an amino acid sequence described herein, via a scFv linker. The light chain variable region and heavy chain variable region of a scFv can be, e.g., in any of the following orientations: light chain variable region-scFv linker-heavy chain variable region or heavy chain variable region-scFv linker-light chain variable region. In some instances, scFvs which bind to a target tumor antigen are prepared according to known methods. For example, scFv molecules can be produced by linking VH and VL regions together using flexible polypeptide linkers. The scFv molecules comprise a scFv linker (e.g., a Ser-Gly linker) with an optimized length and/or amino acid composition. Accordingly, in some embodiments, the length of the scFv linker is such that the VH or VL domain can associate intermolecularly with the other variable domain to form the tumor antigen binding site. In certain embodiments, such scFv linkers are "short", i.e. consist of 0, 1, 2, 3, 4, 5, 6, 7, 8, 9, 10, 11 or 12 amino acid residues. Thus, in certain instances, the scFv linkers consist of about 12 or less amino acid residues. In the case of 0 amino acid residues, the scFv linker is a peptide bond. In some embodiments, these scFv linkers consist of about 3 to about 15, for example 8, 9 or 10 contiguous amino acid residues. Regarding the amino acid composition of the scFv linkers, peptides are selected that confer flexibility, do not interfere with the variable domains as well as allow interchain folding to bring the two variable domains together to form a functional tumor antigen binding site. For example, scFv linkers comprising glycine and serine residues generally provide protease resistance. In some embodiments, linkers in a scFv comprise glycine and serine residues. The amino acid sequence of the scFv linkers can be optimized, for example, by phage-display methods to improve the tumor antigen binding and production yield of the scFv.

In some embodiments, the second domain is from anti-human epidermal growth factor receptor 2 antibody (anti-HER2 antibody), anti-epidermal growth factor receptor antibody (anti-EGFR antibody) or anti-prostate specific membrane antigen antibody (anti-PSMA antibody). In some embodiments, the second domain is anti-HER2 scFv, anti-α-EGFR scFv or anti-PSMA scFv.

In certain embodiments, the third domain (C) which specifically binds to a fibroblast activation protein (FAP) can be any domain that binds to a FAP including, but not limited to, domains from a monoclonal antibody, a polyclonal antibody, a recombinant antibody, a human antibody and a humanized antibody. In one embodiment, the third domain is a single chain variable fragment (scFv) comprising a light chain and a heavy chain of an amino acid sequence provided herein. In one embodiment, the third domain is a scFv, and a light chain variable region comprising an amino acid sequence described herein, is attached to a heavy chain variable region comprising an amino acid sequence described herein, via a scFv linker. The light chain variable region and heavy chain variable region of a scFv can be, e.g., in any of the following orientations: light chain variable region-scFv linker-heavy chain variable region or heavy chain variable region-scFv linker-light chain variable region. In some instances, scFvs which bind to a FAP are prepared according to known methods, as described herein. For example, scFv molecules can be produced by linking VH and VL regions together using flexible polypeptide linkers. The scFv molecules comprise a scFv linker (e.g., a Ser-Gly linker) with an optimized length and/or amino acid composition. Accordingly, in some embodiments, the length of the scFv linker is such that the VH or VL domain can associate intermolecularly with the other variable domain to form the tumor antigen binding site. The certain embodiments of the scFv linkers are those described herein.

The trispecific antigen-binding proteins described herein encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the protein, such as a signal peptide, an internal ribosome entry site, a leader or secretory sequence or a sequence for purification of the protein.

The trispecific antigen-binding proteins described herein are produced by polynucleotide molecules encoding a trispecific antigen-binding protein described herein. The polynucleotide molecules are constructed by known methods such as by combining the genes encoding the three binding domains either separated by peptide linkers or, in other embodiments, directly linked by a peptide bond, into a single genetic construct operably linked to a suitable promoter, and optionally a suitable transcription terminator, and expressing it in bacteria or other appropriate expression system such as, for example cells. In some embodiments, the polynucleotide is inserted into a vector, preferably an expression vector, which represents a further embodiment. This recombinant vector can be constructed according to known methods. Vectors of particular interest include plasmids, phagemids, phage derivatives, virus (e.g., retroviruses, adenoviruses, adeno-associated viruses, herpes viruses, lentiviruses, and the like), and cosmids. A variety of expression vector/host systems may be utilized to contain and express the polynucleotide encoding the polypeptide of the described trispecific antigen-binding protein. The trispecific antigen-binding proteins as described herein, in some embodiments, are produced by introducing a vector encoding the protein as described above into a host cell and culturing said host cell under conditions whereby the protein domains are expressed, may be isolated and, optionally, further purified.

Another aspect of the present invention relates to a nanocarrier comprising a trispecific antigen-binding protein of the invention. In one embodiment, the nanocarrier is encapsulated with a therapeutic drug. In some embodiments, the nanocarrier is liposome or micelle. In some embodiments, the agent may be a small molecule drug, a steroid, an anti-inflammatory agent, a chemotherapeutic, a polypeptide, a protein, an antibody, a vaccine, an enzyme, a nucleic acid, a polynucleotide, a polyribonucleotide, a sensor, and/or a small interfering RNA.

The trispecific antigen-binding protein can enhance the half-life of the therapeutic agent encapsulated within the nanocarrier and enhance the therapeutic effect of the therapeutic agent.

Another aspect of the present invention relates to a pharmaceutical composition comprising a trispecific antigen-binding protein or a nanocarrier of the invention and a pharmaceutically acceptable carrier.

The pharmaceutically acceptable carrier includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

The trispecific antigen-binding proteins or nanocarriers described herein are contemplated for use as a medicament. Administration is effected in different ways, e.g. by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosage for any one patient depends on many factors, including the patient's size, body surface area, age, sex, the particular compound to be administered, time and route of administration, the kind of therapy, general health and other drugs being administered concurrently.

Also provided herein are methods and uses for a treatment of a disease, disorder or condition associated with a tumor or cancer comprising administering to a subject in need thereof a trispecific antigen-binding protein described herein.

Nanocarrier Complex

Described herein are a nanocarrier complex, comprising a nanocarrier conjugated with a plurality of scFv antibodies thereon and pharmaceutical compositions thereof. The nanocarrier complexes of this invention can be used for drug delivery of pharmaceutically-active molecules entrapped within the nanocarrier and/or of pharmaceutically active molecules bound to the carrier system. Moreover, the nanocarrier complexes of this invention has an increased amounts of the antibodies remained on the surface thereof after the nanocarrier complexes are administered to a subject. The conformation of the nanocarrier complexes extend the time of remaining the antibodies conjugated on the surface of the nanocarrier after the nanocarrier complexes are administered to a subject.

Another aspect of the present invention relates to a nanocarrier complex. The nanocarrier complex comprises:
(i) a nanocarrier, optionally encapsulated with a therapeutic agent; and
(ii) a plurality of multispecific antigen-binding scFv antibody, which specifically binds to two or more target antigens and conjugate on the surface of the nanocarrier, wherein the target antigens may be the same or different.

In some embodiments, the nanocarrier is liposome, micelle, a solid or hollow metal nanoparticle or a polymeric nanoparticle. In some embodiments, the therapeutic agent may be a small molecule drug, a steroid, an anti-inflammatory agent, a chemotherapeutic, a polypeptide, a protein, an antibody, a vaccine, an enzyme, a nucleic acid, a polynucleotide, a polyribonucleotide, a sensor, and/or a small interfering RNA. In some embodiment, the agent is selected from the group consisting of anti-inflammatory drugs including: non-steroidal anti-inflammatory drugs (NSAID) and NSAID analogs, indomethacin, sancycline and sancycline analogs, olvanil and olvanil analogs, retro-olvanil and retro-olvanil analogs, olvanil carbamate, NSAID-ache, budesonide and budesonide analogs, methylprenisolone and methylprenisolone analogs and dexamethasone and dexamethasone analogs. Anticancer drugs such as camptothecin, carboplatin, doxorubicin, paclitaxel; HIV Protease Inhibitors including: saquinavir mesylate, amprenavir, ritonavir, indinavir, nelfinavir mesylate, tipranavir, darunavir and atazanavir sulfate; monoclonal antibodies; imaging agents including: coloring dyes like FD and C dyes, or visible/near infrared fluorescence dyes like fluorescein, methylene blue, rhodamine, dansyl, alexa, cyanine dyes, hilyte, indocyanine green and the like.

A target antigen is involved in and/or associated with a disease, disorder or condition. In particular, a target antigen associated with a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease. In some embodiments, a target antigen is a tumor antigen expressed on a tumor cell. Alternatively in some embodiments, a target antigen is associated with a pathogen such as a virus or bacterium.

In some embodiments, a target antigen is a cell surface molecule such as a protein, lipid or polysaccharide. In some embodiments, a target antigen is a on a tumor cell, virally infected cell, bacterially infected cell, damaged red blood cell, arterial plaque cell, or fibrotic tissue cell.

In some embodiments, the multispecific antigen-binding antibody comprises a domain that specifically binds to hapten, wherein the first domain conjugates to the surface of the nanocarrier; and two or more domains specifically binds to two or more target antigens, wherein the target antigens are the same or different. In some embodiments, the multispecific antigen-binding scFv antibody is a bispecific or trispecific antigen-binding scFv antibody. For example, the multispecific antigen-binding scFv antibody comprises (a) a first domain (D) that specifically binds to hapten, wherein the first domain conjugates to the surface of the nanocarrier; (b) a second domain (E) that specifically binds to a first target antigen and is a scFv antibody; and (c) a third domain (F) that specifically binds to a second target antigen and is a scF antibody, wherein the first target antigen and the second target antigen are the same or different. In some embodiments, the antibody comprises (a) a first domain (D) which specifically binds to hapten, comprising a light chain variable region sequence (D-VL) and a heavy chain variable region sequence (D-VH), wherein the first domain conjugates to the surface of the nanocarrier; (b) a second domain (E) which specifically binds to a first target antigen and is a scFv antibody; and (c) a third domain (F) which specifically binds to a second target antigen and is a scFv antibody, wherein the first target antigen and the second target antigen are the same or different, wherein the domains are linked in the order $H_2N$-(D-VL)-(F)-(D-VH)-(E)-COOH or $H_2N$-(D-VL)-(E)-(D-VH)-(F)—COOH.

In some embodiments, the first domain (A), which specifically binds to hapten and comprises a light chain variable region sequence (A-VL) and a heavy chain variable region sequence (A-VH). The first domain (A) conjugates to the surface of the nanocarrier. The first domain (A) may be an anti-hapten antibody or a fragment thereof. In one embodiment, the first domain (A) is an anti-hapten Fab. The examples of hapten are those described herein. The second domain (E) and the third domain (F) are scFv antibodies and specifically binds to the same or different target antigens.

In some embodiments, the second domain an anti-tumor scFv antibody or an anti-FAP antibody. In some embodiments, the third domain an anti-tumor scFv antibody or an anti-FAP antibody. In some embodiments, the anti-tumor scFv antibody is an anti-HER2 scFv antibody, an anti-α-EGFR scFv antibody or an anti-PSMA scFv antibody. In some embodiments, the second or the third domain is the same or different and is selected from an anti-FAP scFv antibody, an anti-HER2 scFv antibody, an anti-α-EGFR scFv antibody and an anti-PSMA scFv antibody.

Another aspect of the present invention relates to a pharmaceutical composition comprising a nanocarrier complex of the invention and a pharmaceutically acceptable carrier.

Also provided herein are methods and uses for a treatment of a disease, disorder or condition comprising administering to a subject in need thereof a nanocarrier complex described herein.

Without limiting the present disclosure, a number of embodiments of the present disclosure are described below for purpose of illustration.

EXAMPLE

Figures 1A, 1B:
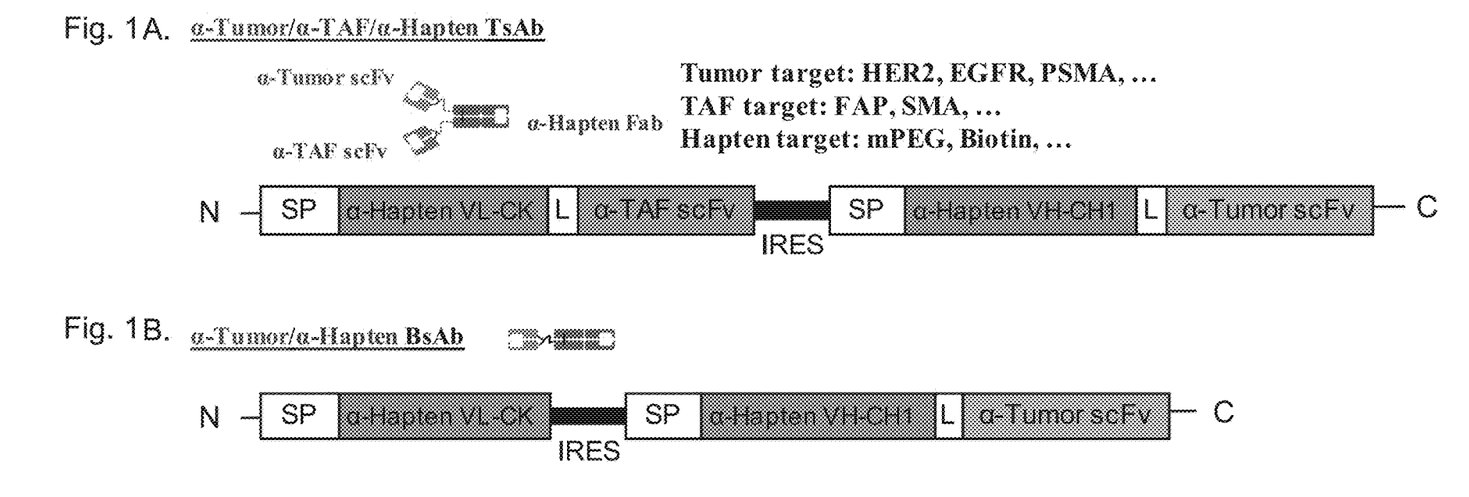
Figure 1C:
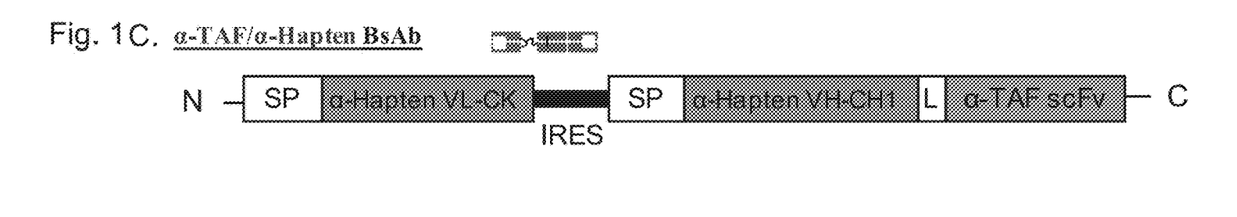

Example 1 Construction of
α-Tumor/α-TAF/α-Hapten TsAb Antibody and
α-Tumor/α-TAF/α-Hapten BsAb Antibody Three antibodies, α-Tumor/α-TAF/α-Hapten TsAb, α-Tumor/α-Hapten BsAb and α-TAF/α-Hapten BsAb, were constructed by genetic engineering. The anti-tumor domains are anti-human epidermal growth factor receptor 2 scFv (α-HER2 scFv), anti-epidermal growth factor receptor scFv (α-EGFR scFv) and anti-prostate specific membrane antigen scFv (α-PSMA scFv), respectively. The α-TAF domain is anti-fibroblast activation protein scFv (α-FAP scFv). The α-Hapten domain is anti-methoxy polyethylene glycol Fab (α-mPEG Fab). The DNA sequences of the α-Tumor scFv domain and the α-TAF scFv domain were linked to the C-terminals of the light chain and the heavy chain of the α-Hapten Fab, respectively, to construct the DNA sequence of α-Tumor/α-TAF/α-Hapten TsAb (see FIG. 1A). The DNA sequences of the α-Tumor scFv domain and the α-TAF scFv domain were linked to the C-terminals of the heavy chain of the α-Hapten Fab, respectively to construct the DNA sequences of α-Tumor/α-Hapten BsAb and α-TAF/α-Hapten BsAb, respectively (see FIGS. 1B and 1C). The above DNA sequences were linked to the expression vector pLNCX.

Figure 2A:
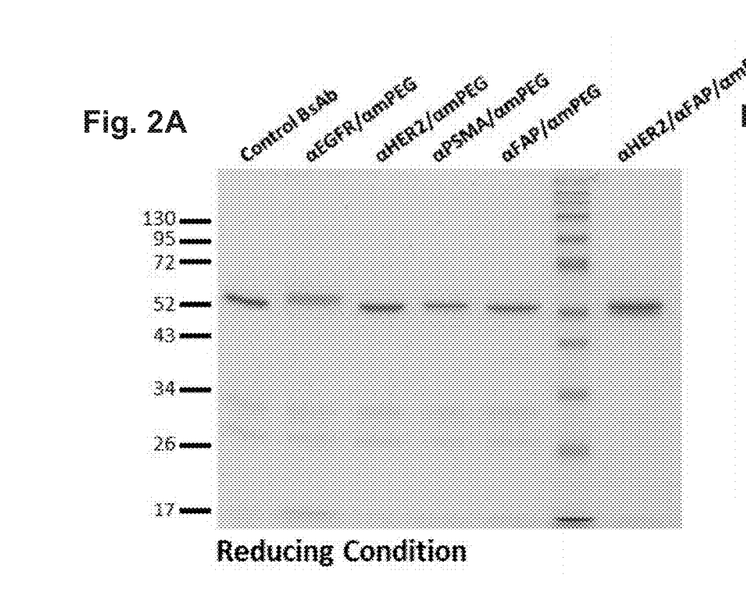
FIGS. 2A and 2B show the SDS PAGE assay of TsAb and BsAb.
Figure 2B:
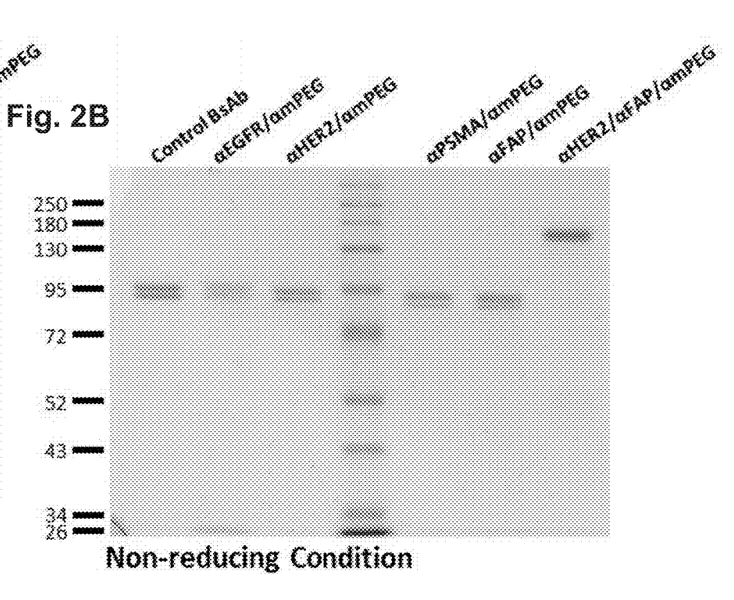
Figure 3A:
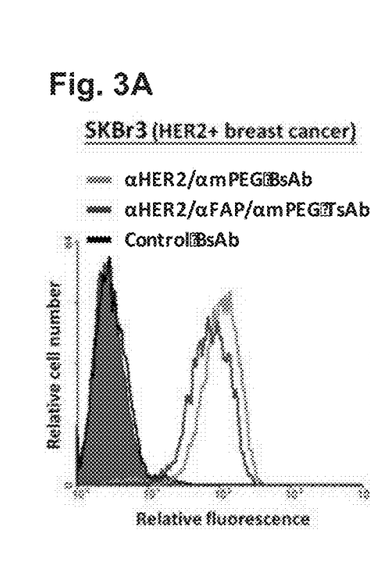
FIGS. 3A to 3D show the binding specificity and capability of BsAb and TsAb to the tumor cells and the tumor-associated fibroblasts.
Figure 3B:
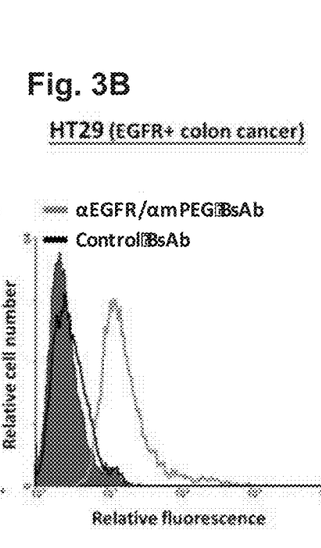
Figure 3C:
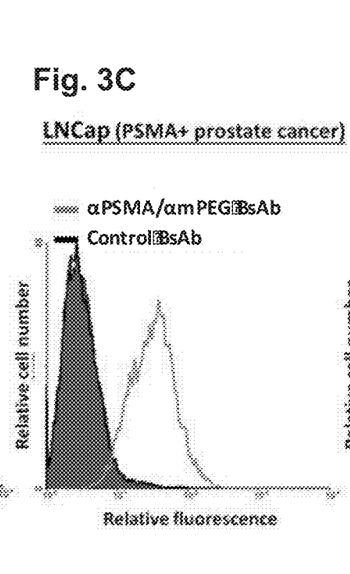
Figure 3D:
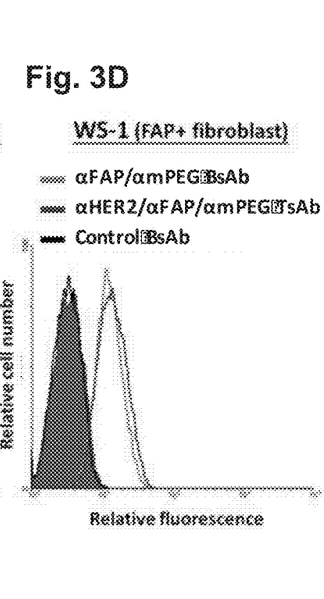

Example 2 Mass Production of
α-Tumor/α-TAF/α-Hapten TsAb Antibody and
α-Tumor/α-TAF/α-Hapten BsAb Antibody The vectors of Example 1 were transfected to Expi293™ Expression System (Invitrogen) to produce antibodies with a yield of 100 mg/L. The resulting antibodies were purified by HisTrap™ HP column (GE Healthcare) and quantified by sodium dodecyl sulfate polyacrylamide gel electrophoresis (SDS-PAGE) to obtain protein purity and molecular weight. It was shown that the light chain and the heavy chain of the TsAb (α-HER2/α-FAP/α-mPEG) have a molecular weight of 52 kDa and that the light chain and the heavy chain of the BsAb (α-EGFR/α-mPEG, α-HER2/α-mPEG, α-PSMA/α-mPEG, α-FAP/α-mPEG and the control) are 30 kDa and 52 kDa, respectively. Therefore, the expression platform can correctly express the TsAb and BsAb antibodies (FIG. 2A). In a non-reducing condition, the molecular weights of TsAb and BsAb are around 150 kDa and 95 kDa, respectively, which shows that the resulting TsAb and BsAb correctly construct as antibodies (see FIG. 2B).

Figure 4:
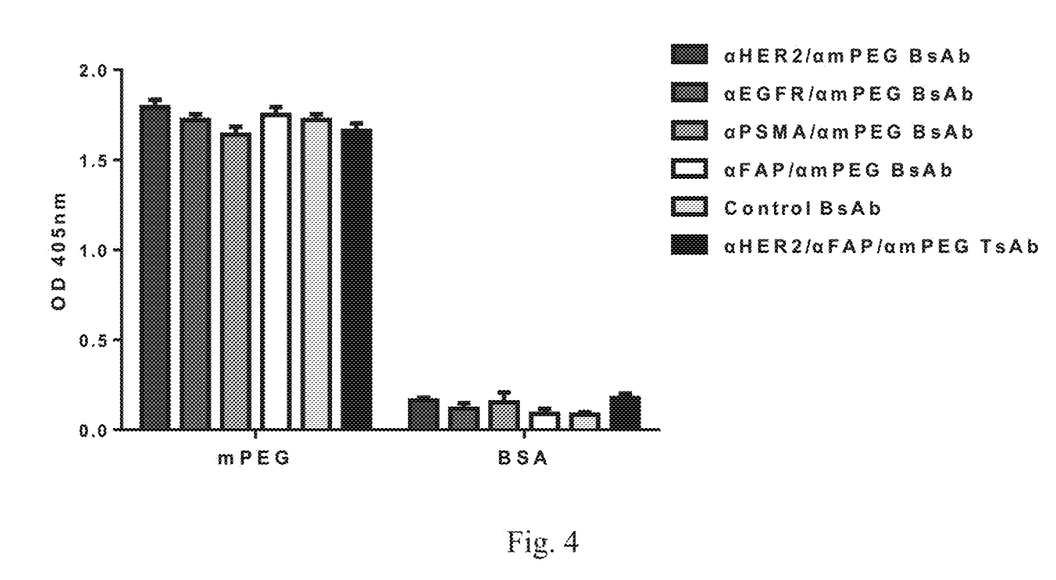

Example 3 Evaluation of Binding of TsAb and
BsAb to Tumor Cells, Tumor-Associated
Fibroblasts or mPEG The binding of TsAb and BsAb to tumor cells and tumor-associated fibroblasts was measured by flow cytometry. FIG. 3 shows that α-HER2/α-FAP/α-mPEG TsAb and α-HER2/α-mPEG BsAb can specifically bind to $HER2^+$ SKBR3 cells, α-EGFR/α-mPEG BsAb can specifically bind to $EGFR^+$HT29 cells, α-PSMA/α-mPEG BsAb can specifically bind to $PSMA^+$ LNCap cells, and α-HER2/α-FAP/α-mPEG TsAb and α-FAP/α-mPEG BsAb can specifically bind to FAP human fibroblasts (WS-1). The control BsAb cannot bind to any cells. The binding abilities of TsAb and BsAb to mPEG were evaluated by Enzyme-linked immunosorbent assay (ELISA). FIG. 4 shows that TsAb and BsAb can specifically bind to mPEG. In addition, TsAb and BsAb do not bind to bovine serum albumin (BSA). The above-mentioned results show that the antibody fragments of TsAb and BsAb can specifically bind to the antigen.

Figure 5:
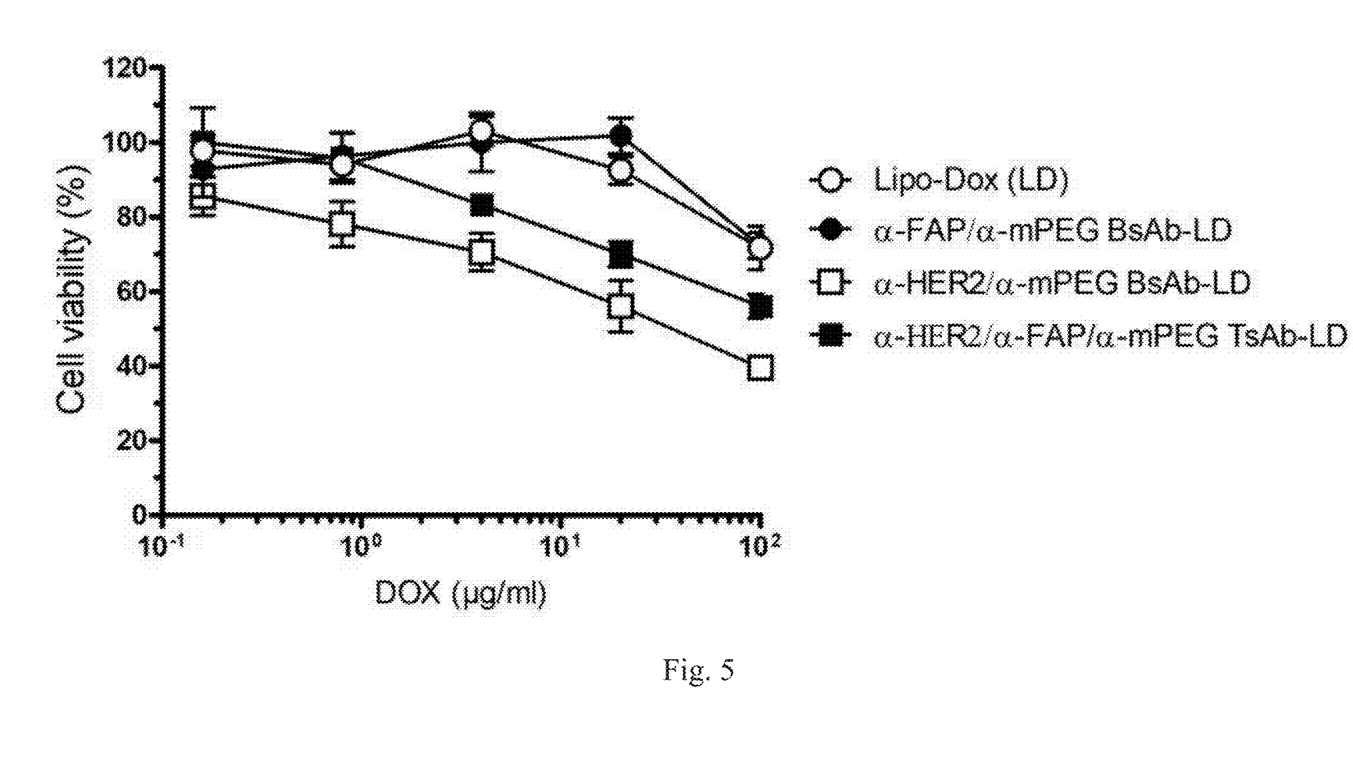

Example 4 the α-HER2/α-FAP/α-mPEG TsAb and
BsAb Enhance the Ability of the
mPEG-Nanocarrier with Drug in Killing Tumor
Cells The α-HER2/α-FAP/α-mPEG TsAb and α-HER2/α-mPEG BsAb were reacted with Lipo-Dox to evaluate whether Lipo-Dox loaded with the α-HER2/α-FAP/α-mPEG TsAb and α-HER2/α-mPEG BsAb have an enhanced ability in killing $HER2^+$ MCF7/HER2 cells. The results show that the α-HER2/α-mPEG BsAb and the α-HER2/α-FAP/α-mPEG TsAb can significantly increase the efficiency of Lipo-Dox in killing MCF7/HER2 cells (FIG. 5).

Figure 6:
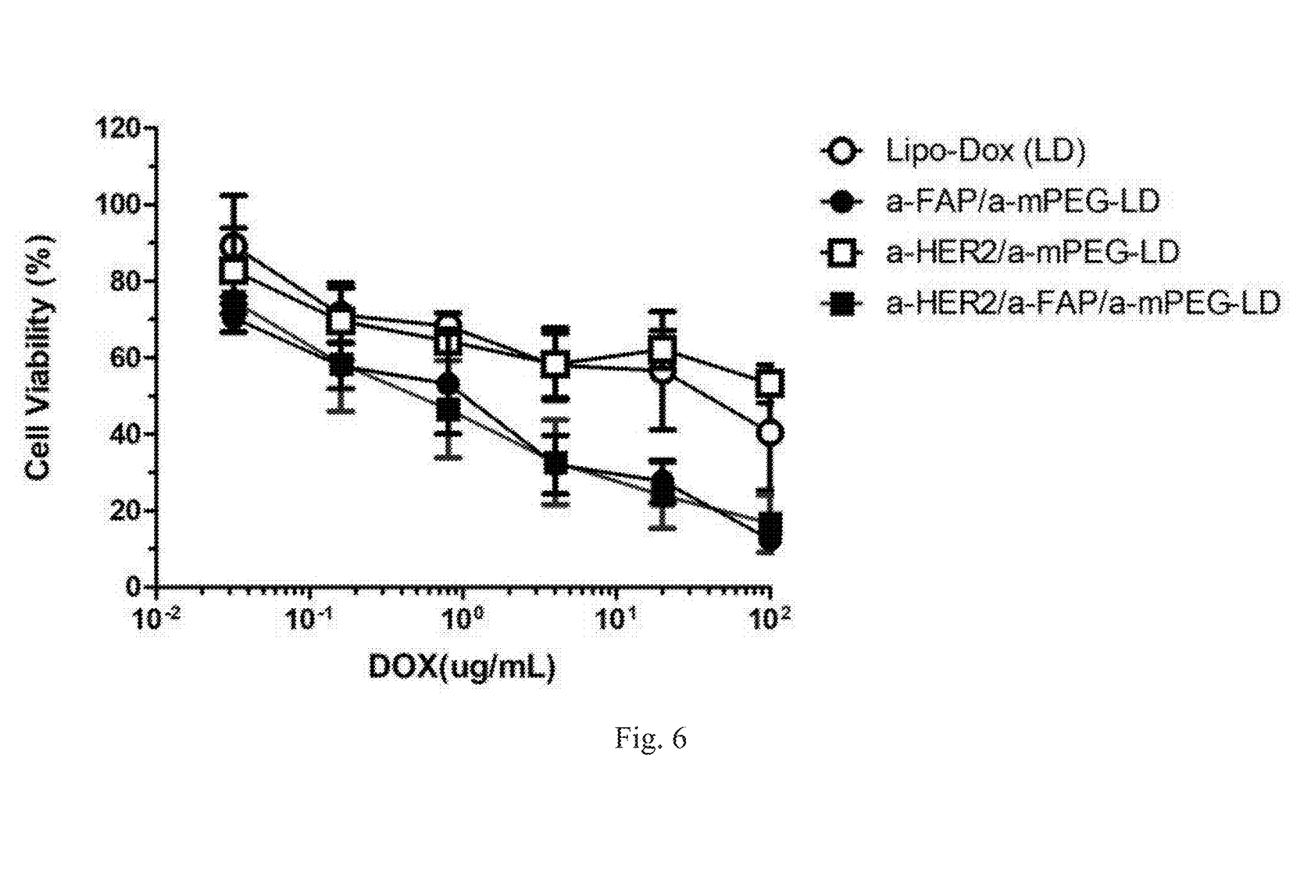

Example 5 the α-HER2/α-FAP/α-mPEG TsAb and
BsAb Enhance the Ability of the
mPEG-Nanocarrier with Drug in Killing FAP
Tumor-Associated Fibroblasts The α-HER2/α-FAP/α-mPEG TsAb and α-HER2/α-mPEG BsAb were reacted with Lipo-Dox to evaluate whether Lipo-Dox loaded with the α-HER2/α-FAP/α-mPEG TsAb and α-HER2/α-mPEG BsAb have an enhanced ability in killing WS-1/FAP cells. The results show that the α-HER2/α-mPEG BsAb and the α-HER2/α-FAP/α-mPEG TsAb can significantly increase the efficiency of Lipo-Dox in killing WS-1/FAP cells (FIG. 6).

Figure 7A:
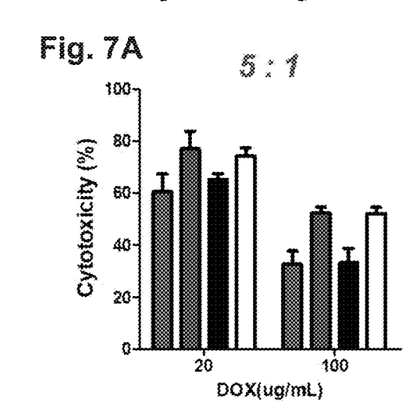
FIGS. 7A to 7C show that the in vitro comparison of TsAb-Lipo-Dox and BsAb-Lipo-Dox in killing breast cancer tissue (co-culture of breast cancer cells and tumor-associated fibroblasts). Various BsAbs and TsAbs were mixed with Lipo-Dox (molar ratio of BsAb:Lipo-Dox (with surface mPEG)=1:200) and reacted in DMEM for 1 hour. TsAb-Lipo-Dox, BsAb-Lipo-Dox and Lipo-Dox in different concentrations were added to human breast cancer tissue (cell number ratio of MCF7/HER2 breast cancer cells:WS1/hFAP fibroblasts=5:1 (FIG. 7A), 1:1 (FIG. 7B), 1:5 (FIG. 7C)), respectively and cultured in DMEM medium at 37° C. for one hour. Fresh DMEM medium (containing 10% CCS) was added to the tissue for replacing the old medium and then cultured for 72 hours. ATPlite kit (Perkin-Elmer) and Top Count NXT (Packard Instruments Company) were used to measure the viability of the breast cancer tissue. Bar, SD.
Figure 7B:
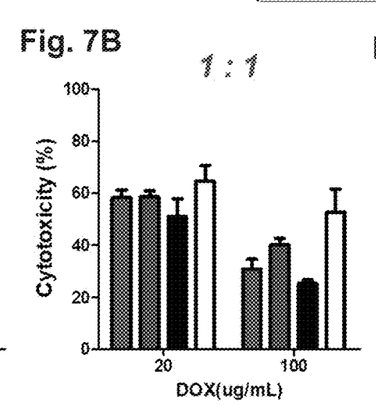
Figure 7C:
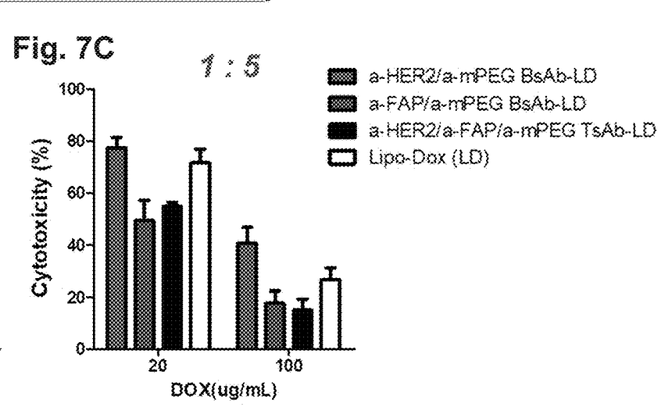

Example 6 the α-HER2/α-FAP/α-mPEG TsAb-Lipo-Dox Enhance the Ability of the mPEG-Nanocarrier with Drug in Killing Tissue Co-Cultured with HER$^+$ Tumor Cells and FAP Tumor-Associated Fibroblasts HER2$^+$ MCF7/HER2 cells and FAP+WS1/hFAP cells were co-cultured in various ratios of MCF7/HER2:WS1/hFAP=5:1, 1:1 and 1:5 to form breast cancer co-culture tissues. The α-HER2 BsAb-Lipo-Dox, α-FAP BsAb-Lipo-Dox and α-HER2/α-FAP TsAb-Lipo-Dox in different concentrations were added to the co-culture tissues. When MCF7/HER2:WS1/hFAP is 5:1, Lipo-Dox and α-FAP BsAb-Lipo-Dox can kill around 48% of the breast cancer tissues at 100 μg/mL of Lipo-Dox, whereas α-HER2/α-FAP TsAb-Lipo-Dox and α-HER2 BsAb-Lipo-Dox can kill up to 67% of the breast cancer tissues (FIG. 7A). When MCF7/HER2:WS1/hFAP is 1:1, Lipo-Dox, α-FAP BsAb-Lipo-Dox, α-HER2 BsAb-Lipo-Dox and α-HER2/α-FAP TsAb-Lipo-Dox can kill around 47.5%, 69.4% 60.1%, and 74.8% of the breast cancer tissues, respectively (FIG. 7B). When MCF7/HER2:WS1/hFAP is 1:5, Lipo-Dox can kill around 73.5% of the breast cancer tissues and α-FAP BsAb-Lipo-Dox as well as α-HER2/α-FAP TsAb-Lipo-Dox can kill 82.5% and 85% of the breast cancer tissue, respectively, whereas α-HER2 BsAb-Lipo-Dox only can kill 59.5% of the breast cancer tissues (FIG. 7C). The above results show that the α-HER2/α-FAP TsAb-Lipo-Dox has the best efficacy in killing cancer tissues in various ratios of the tumor cells and the tumor-associated fibroblasts in a tissue.

Figure 8:
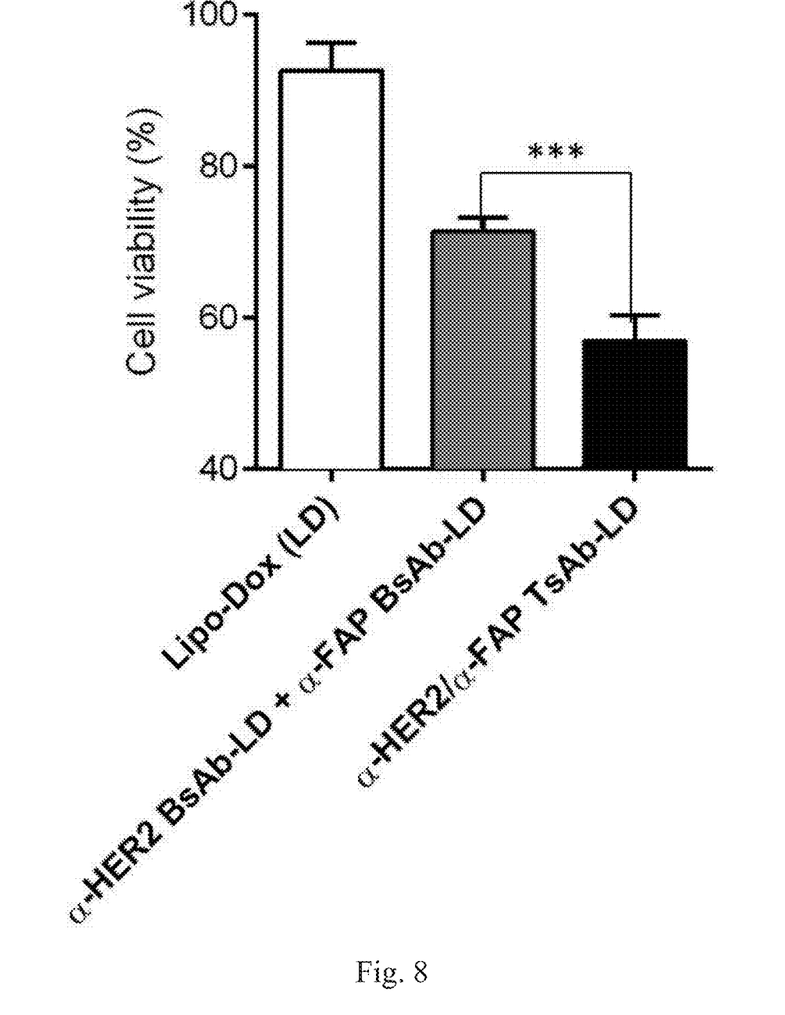
FIG. 8 shows the in vitro cytotoxicity of TsAb-Lipo-Dox and a mixture of α-HER2/α-mPEG BsAb-Lipo-Dox and α-FAP/α-mPEG BsAb-Lipo-Dox. Various BsAbs and TsAbs were mixed with Lipo-Dox (molar ratio of BsAb:Lipo-Dox (with surface mPEG)=1:200) and reacted in DMEM for 1 hour. TsAb-Lipo-Dox (20 μg/ml), and the mixture of α-HER2/α-mPEG BsAb-Lipo-Dox (10 μg/ml) and α-FAP/α-mPEG BsAb-Lipo-Dox (10 μg/ml) were added to a 96-well plate with human breast cancer tissue (MCF7/HER2 breast cancer cells (3000 cells/well) and WS1/hFAP fibroblasts (1000 cells/well), respectively, and cultured in DMEM medium at 37° C. for one hour. Fresh DMEM medium (containing 10% CCS) was added to the tissue for replacing the old medium and then cultured for 72 hours. ATPlite kit (Perkin-Elmer) and Top Count NXT (Packard Instruments Company) were used to measure the viability of the breast cancer tissue. Bar, SD.

Example 7 Cytotoxicity of the α-HER$^2$/α-FAP TsAb-Lipo-Dox on the Tissue Co-Cultured with HER$^+$ Tumor Cells and FAP Tumor-Associated Fibroblasts 20 μg/mL of each of Lipo-Dox, α-HER2/α-FAP/α-mPEG TsAb-Lipo-Dox, and a mixture of α-HER2/α-mPEG BsAb-Lipo-Dox and α-FAP/α-mPEG BsAb-Lipo-Dox (in an amount of 50% and 50%) were added to the breast cancer tissue co-cultured with (HER2$^+$ human breast cancer cells (MCF7/HER2) and FAP fibroblasts (WS1/hFAP)). FIG. 8 shows that Lipo-Dox only kills 7.5% of the breast cancer tissue, whereas the mixture of α-HER2/α-mPEG BsAb-Lipo-Dox and α-FAP/α-mPEG BsAb-Lipo-Dox can kill 28.7% of the breast cancer tissue and α-HER2/α-FAP/α-mPEG TsAb-Lipo-Dox increases 43.1% cytotoxicity on the breast cancer tissue. The results prove that α-HER2/α-FAP/α-mPEG TsAb-Lipo-Dox simultaneously targets and kills breast cancer cells and FAP fibroblasts.

Figure 9:
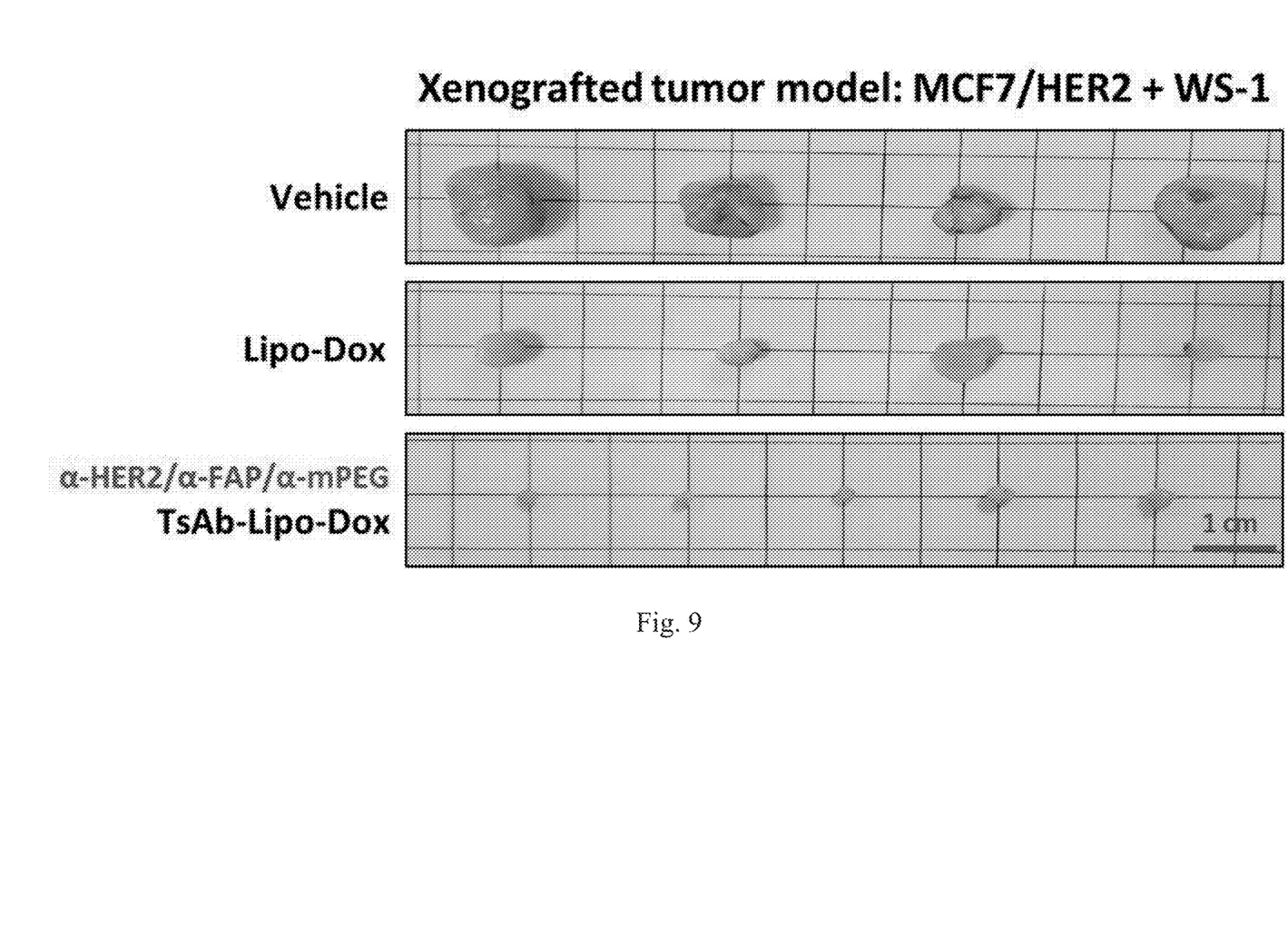
FIG. 9 shows the tumor inhibition effect of TsAb-Lipo-dox on the nude mice with the subcutaneous solid tumor comprising breast cancer tumor cells and FAP fibroblasts. The MCF-7/HER2 cells and WS1/hFAP cells were subcutaneously injected to the nude mice. After the tumor grew to 50 $mm^3$, vehicle (PBS), Lipo-Dox and α-HER2/α-FAP/α-mPEG TsAb-Lipo-Dox were administered to the mice once a week at a dose of 5 mg/kg Lipo-Dox through intravenous injection, tail vein. The solid tumor was taken at the ninth week to measure the size thereof.

Example 8 Efficacy of α-HER2/α-FAP/α-mPEG TsAb-Lipo-Dox Nanocarrier Drug on the Subcutaneous Solid Tumor Comprising Breast Cancer Tumor Cells and FAP Fibroblasts MCF-7/HER2 cells and WS1/hFAP cells were mixed and subcutaneously injected to nude mice to form tumors. Then, α-HER2/α-FAP/α-mPEG TsAb and Lipo-Dox were administered to the mice by injection. FIG. 9 shows that the tumor size of the Lipo-Dox group is 28.5% of the control group and that of the α-HER2/α-FAP/α-mPEG TsAb group is 8.3% of the control group. The results prove that TsAb-Lipo-Dox can effectively reduce the size of the xenogeneic solid tumor.

Figure 10A:
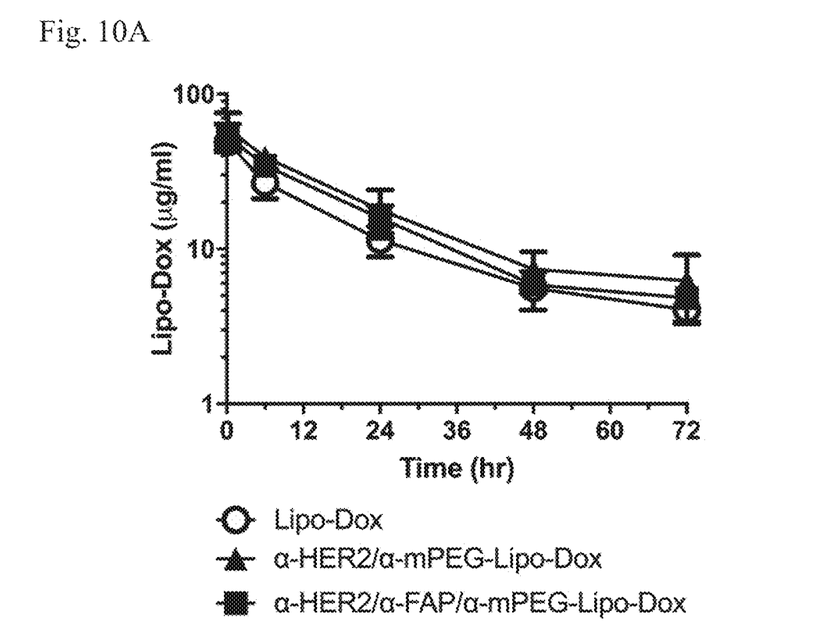
FIGS. 10A and 10B show the half-life of TsAb-Lipo-Dox, BsAb-Lipo-Dox and Lipo-Dox in mice and the remaining antibodies on the surface of the liposome after administration.

Example 9 Efficacy of α-HER2/α-FAP/α-mPEG TsAb in Increasing In Vivo Half-Life of Lipo-Dox and Increasing Amounts of the Antibodies Remained on the Surface of Liposome The α-HER2/α-FAP/α-mPEG TsAb-Lipo-Dox, α-HER2/α-mPEG B sAb-Lipo-Dox and Lipo-Dox were administered to mice through intravenous injection, tail vein. The blood samples were taken at different time points to measure the amounts of Lipo-Dox in serum. FIG. 10A shows that the half-life of the α-HER2/α-FAP/α-mPEG-Lipo-Dox (10 hours) is higher than that of Lipo-Dox (6.6 hours).

Figure 10B:
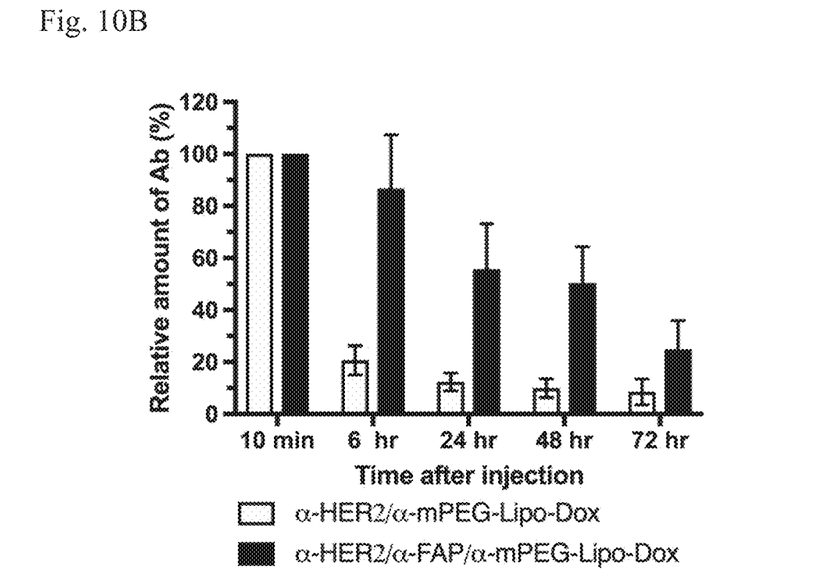

The α-HER2/α-FAP/α-mPEG TsAb-Lipo-Dox, α-HER2/α-mPEG B sAb-Lipo-Dox and Lipo-Dox were administered to mice through intravenous injection, tail vein. The blood samples were taken at different time points to measure the amounts of Lipo-Dox in serum. The remaining amounts of TsAb on the liposome at different time points were measured. FIG. 10B shows that after 6, 24, 48, and 72 hours, the TsAb amounts remained on the surface of α-HER2/α-FAP/α-mPEG TsAb-Lipo-Dox are much higher than that on the surface of α-HER2/α-mPEG BsAb-Lipo-Dox (24.9% vs. 8.5% at 72 hour).

Figure 11:
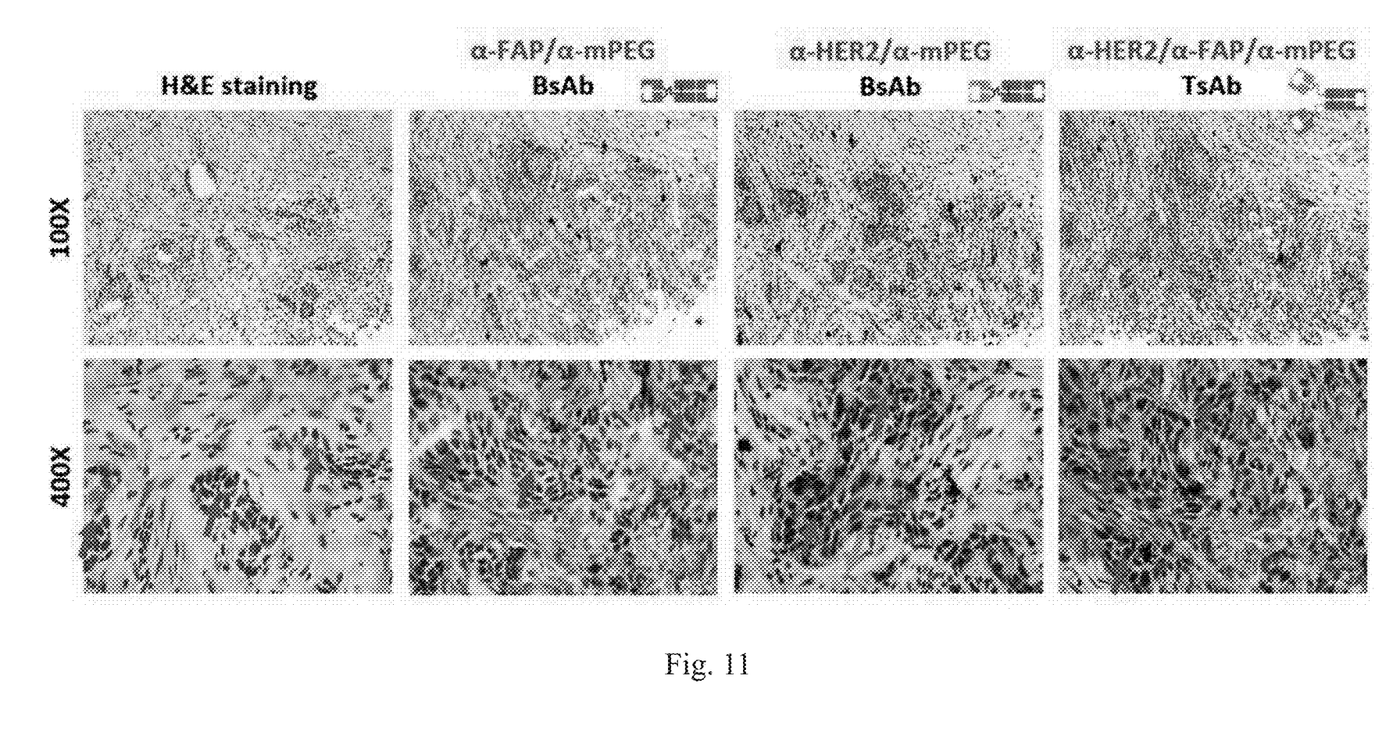
FIG. 11 shows that α-HER2/α-FAP/α-mPEG TsAb and BsAb can specifically target tumor cells and FAP fibroblasts. TsAb and BsAb were reacted with $HER2^+$ breast cancer tissues. Then, the biotin-secondary antibody was added to react with streptavidin-HRP. DAB was used in immunohis-

Example 10 Specifically Targeting Tumor Cells and FAP Fibroblasts in Human Breast Cancer Tissue by α-HER$^2$/α-FAP/α-mPEG TsAb and BsAb TsAb and BsAb were reacted with HER2$^+$ breast cancer tissues to detect the specificity of the antibodies. FIG. 11 shows that α-HER2/α-mPEG BsAb and α-HER2/α-FAP/α-mPEG TsAb cam specifically recognize HER2$^+$ tumor cells and FAP fibroblasts. The results prove that α-HER2/α-FAP/α-mPEG TsAb and BsAb can specifically target tumor cells and FAP fibroblasts.

What is claimed is:

1. A trispecific antigen-binding protein, comprising (a) a first domain (A) that specifically binds to hapten, comprising a light chain variable region sequence and a heavy chain variable region sequence; (b) a second domain (B) that specifically binds to a target tumor antigen; and (c) a third domain (C) that specifically binds to a fibroblast activation protein (FAP), wherein the domains are linked in the order H$_2$N-(A)-(C)-(B)—COOH or H$_2$N-(A)-(B)-(C)—COOH;
    wherein the hapten is conjugated to mPEG;
    wherein the domain (B) is from an anti-human epidermal growth factor receptor 2 (anti-HER2) monoclonal antibody, an anti-epidermal growth factor receptor (anti-EGFR) monoclonal antibody or an anti-prostate specific membrane antigen (anti-PSMA) monoclonal antibody; and
    wherein the domain (C) is from an anti-FAP monoclonal antibody.

2. The trispecific antigen-binding protein of claim 1, wherein the domain (B) is a single chain variable fragment (scFv).

3. The trispecific antigen-binding protein of claim 1, wherein the domain (B) is anti-HER2 scFv, anti-α-EGFR scFv or anti-PSMA scFv.

4. The trispecific antigen-binding protein of claim 1, wherein the domain (C) is a single chain variable fragment (scFv).

5. The trispecific antigen-binding protein of claim 1, which further comprises a signal peptide and/or an internal ribosome entry site.

6. A nanocarrier comprising a trispecific antigen-binding protein of claim 1.

7. The nanocarrier of claim 6, wherein the nanocarrier is encapsulated with a therapeutic drug.

8. The nanocarrier of claim 6, which is a liposome or micelle.

9. A pharmaceutical composition comprising a trispecific antigen-binding protein of claim 1 and a pharmaceutically acceptable carrier.

10. A pharmaceutical composition comprising a nanocarrier of claim 6 and a pharmaceutically acceptable carrier.

11. A method for treating a cancer, comprising administering a trispecific antigen-binding protein of claim 1 to a subject.

12. A method for treating a cancer, comprising administering a nanocarrier of claim 6 to a subject.

* * * * *